United States Patent [19]

Kehne

[11] Patent Number: 5,284,945
[45] Date of Patent: Feb. 8, 1994

[54] PROCESS FOR THE PREPARATION OF 2-PYRIDYLSULFONYLUREAS

[75] Inventor: Heinz Kehne, Hofheim am Taunus, Fed. Rep. of Germany

[73] Assignee: Hoechst Aktiengesellschaft, Frankfurt am Main, Fed. Rep. of Germany

[21] Appl. No.: 23,623

[22] Filed: Feb. 26, 1993

Related U.S. Application Data

[62] Division of Ser. No. 866,002, Apr. 9, 1992, Pat. No. 5,235,050.

[30] Foreign Application Priority Data

Apr. 11, 1991 [DE] Fed. Rep. of Germany ....... 4111800

[51] Int. Cl.$^5$ ............................................ C07D 401/12
[52] U.S. Cl. .................... 544/212; 544/207; 544/209; 544/198; 544/320; 544/324; 544/331; 544/113; 544/122; 544/123; 544/96; 544/63
[58] Field of Search ............... 544/212, 207, 209, 198, 544/320, 324, 331, 113, 122, 123, 96, 63

[56] References Cited

U.S. PATENT DOCUMENTS 4,789,393  12/1988  Hanagan ............................ 544/320

FOREIGN PATENT DOCUMENTS 0013480  7/1980  European Pat. Off. .
0021641  1/1981  European Pat. Off. .
0184385  6/1986  European Pat. Off. .
0336354  6/1986  European Pat. Off. .
0308371  3/1989  European Pat. Off. .
0317336  5/1989  European Pat. Off. .
0451468  10/1991  European Pat. Off. .
4000503  7/1991  Fed. Rep. of Germany .
WO 87/07114  12/1987  PCT Int'l Appl. .
WO 89/04297  6/1988  PCT Int'l Appl. .
WO 89/02700  4/1989  PCT Int'l Appl. .

Primary Examiner—John M. Ford
Attorney, Agent, or Firm—Curtis, Morris & Safford

[57] ABSTRACT

The process according to the invention for the preparation of herbicidal pyridylsulfonylureas of the formula (I)

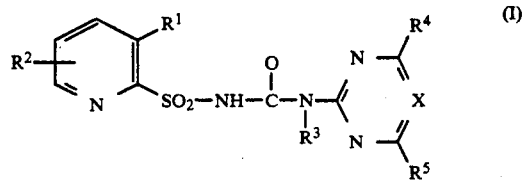

in which $R^1$ to $R^5$ and X are as defined in claim 1 comprises the reaction of the zwitterion (II) with the amino heterocycle (III)

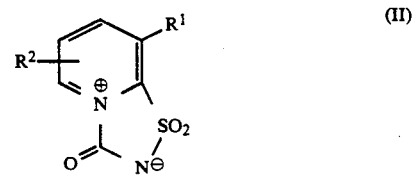

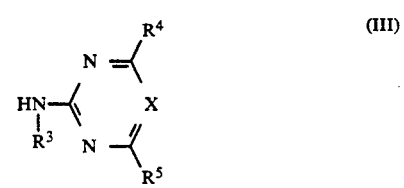

The novel zwitterionic 1,1,3-trioxo-1,2,4-thiadiazolo[4,5-a]pyridines can be obtained according to the invention by the reaction of phosgene with compounds IV, or the reaction of phosgene with compounds V

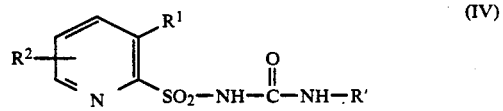

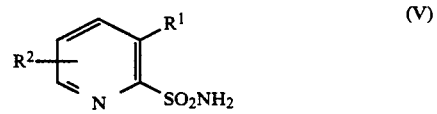

in the presence of an alkyl isocyanate.

6 Claims, No Drawings

PROCESS FOR THE PREPARATION OF 2-PYRIDYLSULFONYLUREAS

This application is a division of application Ser. No. 07/866,002, filed Apr. 9, 1992, now U.S. Pat. No. 5,235,050.

DESCRIPTION

2-Pyridylsulfonylureas are known herbicides with a wide range of potential uses. Important representatives of this substance class and their preparation and use are known, for example, from EP-A-184,385, WO 89/02700, WO 88/04297 or DE-A-4,000,503 (ZA 91/0173).

However, the preparation processes disclosed in these publications are not ideal. Particular disadvantages are the low yields, the use of expensive catalysts, or catalysts which are difficult to manipulate such as, for example, 1,8-diazabicyclo[5.4.0]undec-7-ene (DBU) or trimethylaluminum, the limited range within which the reactions can be carried out, or the use of educts or reagents in large excess.

It is the object of the present invention to provide a simple, economical process which can be carried out on an industrial scale while reducing, or avoiding, the described disadvantages.

The present invention therefore relates to a process for the preparation of compounds of the formula (I)

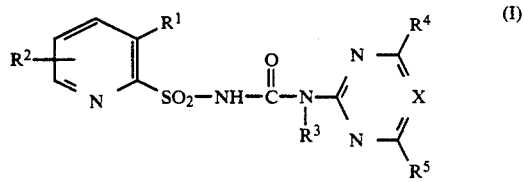

in which $R^1$ is $(C_1-C_4)$alkyl, which is unsubstituted or substituted by one or more radicals from the group comprising halogen, hydroxyl, $(C_1-C_4)$alkoxy, $(C_1-C_4)$haloalkoxy and $(C_2-C_8)$alkoxyalkoxy, or is —$COR^6$, $(C_1-C_4)$alkylsulfonyl, halogen, $NO_2$, —$ER^7$, —$NR^8R^9$ or —$SO_2NR^{10}R^{11}$, $R^2$ is H, $(C_1-C_3)$alkyl which is unsubstituted or substituted by $(C_1-C_3)$alkoxy, hydroxyl, $(C_1-C_2)$alkylthio or CN, or is $(C_1-C_3)$haloalkyl, halogen, CN, $NO_2$, $(C_1-C_3)$alkoxy,, $(C_1-C_3)$alkylthio, $(C_1-C_3)$haloalkoxy, $(C_1-C_3)$alkylamino, di$(C_1-C_3)$alkylamino or $(C_1-C_3)$alkylsulfonyl, $R^3$ is H or $CH_3$, $R^4$ and $R^5$ independently of one another are $(C_1-C_3)$alkyl, $(C_1-C_3)$alkoxy, $(C_1-C_3)$haloalkyl, $(C_1-C_3)$haloalkoxy, $(C_1-C_3)$alkylthio, halogen, $(C_2-C_5)$alkoxyalkyl or $(C_1-C_3)$alkylamino, X is CH or N, $R^6$ is H, —$NR^{10}R^{11}$, —$ER^{12}$ or $(C_1-C_4)$alkyl which is unsubstituted or substituted by one or more radicals from the group comprising halogen, $(C_1-C_3)$alkoxy and $(C_1-C_3)$alkylthio, E is an oxygen or sulfur atom, $R^7$ is $(C_1-C_4)$alkyl which is unsubstituted or substituted by one or more radicals from the group comprising halogen, $(C_1-C_3)$alkoxy, $(C_3-C_4)$alkenyloxy, $(C_3-C_4)$alkynyloxy, $(C_1-C_3)$alkylthio and $[(C_1-C_4)$-alkoxy]-carbonyl, or is $(C_3-C_4)$alkenyl or $(C_3-C_4)$alkynyl, $R^8$ is $(C_1-C_4)$alkyl, $(C_1-C_4)$haloalkyl or $(C_2-C_6)$alkoxyalkyl, $R^9$ is $(C_1-C_4)$alkylsulfonyl which is unsubstituted or substituted by one or more radicals from the group comprising halogen and $(C_1-C_4)$alkoxy, $(C_1-C_4)$haloalkyl $R^{10}$ and $R^{11}$ independently of one another are H, $(C_1-C_3)$alkyl, $(C_1-C_3)$haloalkyl, $(C_1-C_2)$alkoxy, $(C_3-C_4)$alkenyl or $(C_3-C_4)$alkynyl, or $R^{10}$ and $R^{11}$ together are an alkylene bridge of the formula —$(CH_2)_n$—, in which n is 2, 3, 4 or 5, it being possible for the alkylene bridge to be interrupted by an oxygen atom, and $R^{12}$ is $(C_1-C_4)$alkyl which is unsubstituted or substituted by one or more radicals from the group comprising halogen, $(C_1-C_3)$alkoxy, $(C_3-C_4)$alkenyloxy, $(C_3-C_4)$alkynyloxy, phenoxy, $(C_1-C_3)$alkylthio or $[(C_1-C_4)$alkoxy]carbonyl, or is $(C_3-C_4)$alkenyl, $(C_3-C_4)$alkynyl or phenyl, which comprises reacting a zwitterionic 1,1,3-trioxo-1,2,4-thiadiazolo[4,5-a]pyridine of the formula (II)

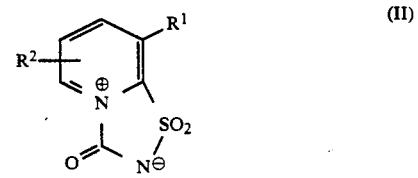

in which $R^1$ and $R^2$ have the same meaning as in formula (I), with an amino heterocycle of the formula (III)

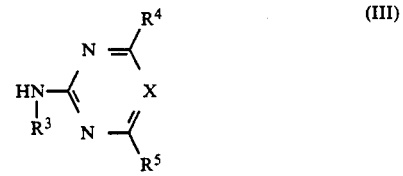

in which $R^3$, $R^4$, $R^5$ and X have the same meaning as in formula (I).

In the abovementioned formulae, alkyl, alkoxy, haloalkyl, alkylamino and alkylthio radicals and the corresponding unsaturated and/or substituted radicals can in each case be straight-chain or branched, unless otherwise indicated. Alkyl radicals, also in composite meanings such as alkoxy, haloalkyl, alkoxycarbonyl, alkoxyalkoxy and the like, are, for example, methyl, ethyl, n- or i-propyl or n-, i-, t- or 2-butyl; alkenyl and alkynyl radicals have the meaning of the unsaturated radicals which are possible and which correspond to the alkyl radicals such as 2-propenyl, 2- or 3-butenyl, 2-propynyl or 2- or 3-butynyl, halogen is fluorine, chlorine, bromine or iodine. Haloalkyl or haloalkoxy are alkyl or alkoxy which are substituted by one or more radicals from the group comprising F, Cl, Br and iodine, preferably fluorine or chlorine.

Of particular importance is the process according to the invention in which $R^1$ is $(C_1-C_4)$alkyl, which is unsubstituted or substituted by one or more halogen atoms or one or two, preferably one, hydroxyl or $(C_1-C_4)$alkoxy or by one or more halogen atoms and one or two, preferably one, hydroxyl or ($C_1$-$C_4$)alkoxy, or is —$COR^6$, ($C_1$-$C_4$)alkylsulfonyl, halogen or —$NR^8R^9$, $R^2$ is H, ($C_1$-$C_3$)alkyl which is unsubstituted or substituted by ($C_1$-$C_3$)alkoxy, hydroxyl, ($C_1$-$C_2$)alkylthio or cyano, ($C_1$-$C_3$)alkylthio, ($C_1$-$C_3$)haloalkoxy, ($C_1$-$C_3$)alkylamino or di($C_1$-$C_3$)alkylamino, $R^3$ is H or $CH_3$, $R^4$ and $R^5$ independently of one another are ($C_1$-$C_2$)alkyl, ($C_1$-$C_3$)alkoxy, ($C_1$-$C_2$)haloalkyl, ($C_1$-$C_2$)haloalkoxy, halogen or ($C_1$-$C_2$)alkylamino, X is CH or N, $R^6$ is H, —$ER^{12}$ or ($C_1$-$C_4$)alkyl, E is an oxygen atom, $R^8$ is ($C_1$-$C_4$)alkyl or ($C_1$-$C_4$)haloalkyl, $R^9$ is ($C_1$-$C_4$)alkylsulfonyl or ($C_1$-$C_4$)haloalkyl and $R^{12}$ is ($C_1$-$C_4$)alkyl.

The reaction of the compounds of the formulae II and III is carried out, for example, in an organic solvent which is inert under the reaction conditions at temperatures from −10° C. up to the boiling point of the solvent, preferably at 0° C. to 80° C. Suitable solvents are, for example, halogenated aliphatic or aromatic hydrocarbons such as dichloromethane or chlorobenzene, aromatic hydrocarbons such as toluene or xylene, ethers such as diethyl ether, dimethoxyethane, diethylene glycol dimethyl ether, dioxane or tetrahydrofuran, esters such as ethyl acetate or butyl acetate, ketones such as acetone or methyl isobutyl ketone, nitriles such as acetonitrile, or amides such as dimethylformamide.

In this context, it is expedient to separately dissolve, or suspend, the educts of the formulae (II) and (III) in the particular solvent, to cool the solutions or suspensions if necessary, and to combine them. The reaction mixture is then stirred at the particular reaction temperature until the reaction is complete. The reaction product of the formula (I) can then frequently simply be filtered off with suction.

Alternatively, it is possible to use other customary methods for working-up and isolating the product. For example, the solvent can generally be removed by distillation and the resulting crude product can, if necessary, be further purified by suitable methods.

While the amino heterocycles of the formula (III) are known from the literature (cf. "The Chemistry of Heterocyclic Compounds" Vol. XVI (1962) and Supplement I and Vol. XIII (1959), Interscience Publ. New York & London), the zwitterionic thiadiazolopyridines of the formula (II) are novel compounds. The present invention therefore also relates to the 1,1,3-trioxo-1,2,4-thiadiazolo[4,5-a]pyridines of the formula (II) and to their preparation. The compounds of the formula (II) are obtained, for example, starting from N-pyridylsulfonyl-N'-alkylureas of the formula (IV)

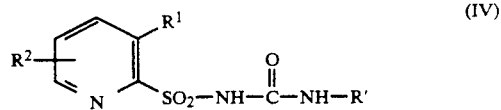

in which $R^1$ and $R^2$ are as defined in the abovementioned formula (I) and R' is ($C_1$-$C_8$)alkyl, by reaction with phosgene. The reaction i preferably carried out in organic solvents which are inert under the reaction conditions such as, for example, aromatic hydrocarbons, for example toluene, xylene or tetralin, or halogenated aromatic hydrocarbons, for example chlorobenzene or dichlorobenzene, at temperatures between 70° C. and the boiling point of the solvent, in particular 70° C. to 140° C. In this context, 1.0–10.0 moles of phosgene are preferably used per mole of alkylsulfonylurea of the formula (IV). To accelerate the reaction, a non-aqueous base, for example an organic amine base, such as a tertiary amine, for example triethylamine or 1,4-diazabicyclo[2.2.2]octane (DABCO), can, if appropriate, be added as catalyst. The alkyl isocyanate, which is formed during the reaction, can be recovered from the reaction mixture by means of distillation, while the product (II) usually precipitates from the solution after cooling and can be isolated by filtration with suction. The yields in this process are generally in an order of magnitude of 90% of theory.

The starting materials of the formula (IV) for the phosgenation reaction are known from the literature or can be prepared by processes known from the literature (cf. Boggiano et al., J. of Pharmacy and Pharmacology 13, 567 (1961), WO 87/07114 or EP-A-336,354).

Compounds of the formula (I) can be prepared from compounds of the formula (IV), for example as a two-step process with isolation of the zwitterionic thiadiazolopyridine of the formula (II) and its subsequent reaction to give the sulfonylurea of the formula (i), or the compound of the formula (II) is not isolated and instead reacted to give the sulfonylurea of the formula (I), by adding, after the formation of (II), the amino heterocycle (III) directly to the reaction mixture of the first step (one-pot reaction).

Furthermore, it is possible, starting from a sulfonamide of the formula (V)

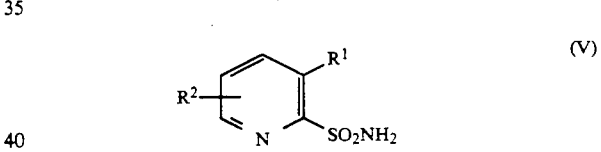

in which $R^1$ and $R^2$ are as defined in formula (I), to carry out the phosgenation step directly in the presence of a ($C_1$-$C_8$)alkyl isocyanate and, if appropriate, one of the abovementioned non-aqueous bases, for example a tertiary amine such as triethylamine or DABCO, as catalyst. In this case, the alkylsulfonylureas of the formula (IV) are not isolated, but only formed in situ and immediately further reacted to give compounds of the formula (II). The compounds of the formula (V) are known (see, for example, WO 88/04297, DE-A-4,000,503 (ZA 91/0173)).

The following examples are intended to illustrate the process according to the invention in greater detail:

EXAMPLE 1

7-(N-Methyl-N-methylsulfonyl-amino)-1,1,3-trioxo-1,2,4-thiadiazolo[4,5-a]pyridine of the formula (II-1)

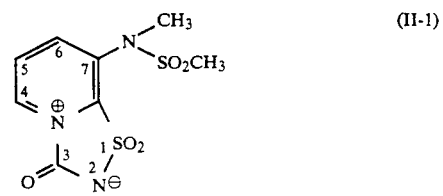

36.5 g (0.1 mol) of 3-butyl-1-[3-(N-methyl-N-methylsulfonyl-amino)-2-pyridylsulfonyl]urea are suspended in 600 ml of chlorobenzene, and the suspension is heated to 70° C. At this temperature, the experiment starts to pass a gentle stream of phosgene into the suspension, and heating is continued for approx. 20 minutes until an internal temperature of 120° C. is reached. After phosgene is passed in for another 20 minutes (approx. 30 g (0.3 mol) of phosgene in total), the lower-boiling components together with approx. 30% of the solvent are removed from the reaction mixture by distillation over a period of 20 minutes. After the mixture has been cooled to room temperature and filtered and the solid has been washed with diethyl ether, 26.7 g (92% of theory) of the compound of the formula (II-1) of m.p. 208°–209° C. (decomp.) are obtained.

$^1$H NMR (80 MHz, d$_6$-DMSO): δ [ppm]=8.40 (dd, J$^1$=9 Hz, J$^2$=7 Hz; 1H, 5-H), 8.95 (d, J=9 Hz; 1H, 6-H), 9.35 (d, H=7 Hz; 1H, 4-H).

IR (KBr): ν=1810 cm$^{-1}$ (C=O), no signal between 2200 and 2300 cm$^{-1}$.

The compounds of the formula II which are listed in Table 1 are also obtained similarly to Example 1.

TABLE 1

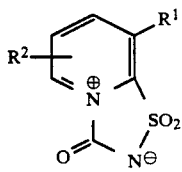

| Compound No. | R$^1$ | R$^2$ | M.p. [°C.] |
|---|---|---|---|
| II-1 | —N(CH$_3$)SO$_2$CH$_3$ | H | 208–209 (decomp.) |
| II-2 | " | 4-Cl | |
| II-3 | " | 5-Cl | |
| II-4 | " | 6-Cl | |
| II-5 | " | 4-CH$_3$ | |
| II-6 | " | 5-CH$_3$ | |
| II-7 | " | 6-CH$_3$ | 105–108 (decomp.) |
| II-8 | " | 4-OCH$_3$ | |
| II-9 | —N(C$_2$H$_5$)SO$_2$CH$_3$ | H | |
| II-10 | —N(CH$_3$)SO$_2$C$_2$H$_5$ | H | |
| II-11 | —N(CHF$_2$)SO$_2$CH$_3$ | H | |
| II-12 | —N(CH$_3$)SO$_2$CF$_3$ | H | |
| II-13 | —(CH$_2$CH$_2$Cl)SO$_2$CH$_3$ | H | |
| II-14 | Cl | H | |
| II-15 | Br | H | |
| II-16 | I | H | 241–242 (decomp.) |
| II-17 | —SO$_2$CH$_3$ | H | |
| II-18 | —SO$_2$C$_2$H$_5$ | H | 181–182 (decomp.) |
| II-19 | —SO$_2$C$_3$H$_7$ | H | |
| II-20 | —CO$_2$CH$_3$ | H | 185–186 |
| II-21 | —CO$_2$C$_2$H$_5$ | H | |
| II-22 | —CO$_2$C$_4$H$_9$ | H | |
| II-23 | —CF$_3$ | H | |
| II-24 | —SO$_2$N(CH$_3$)$_2$ | H | |
| II-25 | —OC$_2$H$_5$ | H | |
| II-26 | —OCHF$_2$ | H | |
| II-27 | —CO$_2$CH$_3$ | 4-CH$_2$OCH$_3$ | |
| II-28 | " | 4-CH$_2$SCH$_3$ | |
| II-29 | " | 4-CH$_2$CN | |
| II-30 | " | 4-CF$_3$ | |
| II-31 | " | 3-SCH$_3$ | |
| II-32 | " | 4-OCH$_2$CF$_3$ | |
| II-33 | " | 4-N(CH$_3$)$_2$ | |
| II-34 | " | 4-CN | |

EXAMPLE 2

7-(N-Methyl-N-methylsulfonyl-amino)-1,1,3-trioxo-1,2,4-thiadiazolo[4,5-a]pyridine of the formula (II-1) starting from the corresponding sulfonamide A solution of 26.5 g (0.1 mol) of 3-(N-methyl-N-methylsulfonylamino)-2-pyridylsulfonamide, 10.0 g (0.1 mol) of butyl isocyanate and 0.1 g of 1,4-diazabicyclo[2.2.2]octane in 150 ml of chlorobenzene is refluxed for 20 minutes. Phosgene is then passed in for 1 hour, also at reflux temperature. After the lower-boiling components have been removed by distillation under atmospheric pressure, the mixture is cooled to room temperature, and the solid is filtered off. After washing with diethyl ether, 25.0 g (86% of theory) of the compound (II-1), which has the same physical properties as described in Example 1, are obtained.

EXAMPLE 3

3-(4-Methoxy-6-methyl-1,3,5-triazin-2-yl)-3-methyl-1-[3-(N-methyl-N-methylsulfonylamino)-2-pyridyloulfonyl]-urea 2.9 g (10 mmol) of the compound (II-1) (Example 1) and 1.6 g (10.5 mmol) of 4-methoxy-6-methyl-2-methylamino-1,3,5-triazine are combined in 100 ml of dichloromethane, and the mixture is refluxed for 24 hours. The mixture is then cooled, the organic phase is washed once using 50 ml each of 1N HCl and water, dried and evaporated to dryness. After the crude product has been triturated with diethyl ether, there remain 3.9 g (88% of theory) of 3-(4-methoxy-6-methyl-1,3,5-triazin-2-yl)-3-methyl-1-[3-(N-methyl-N-methylsulfonyl-amino)-2-pyridylsulfonyl)-urea of m.p. 142°–144° C. (decomp.).

EXAMPLE 4

3-(4,6-Dimethoxypyrimidin-2-yl)-1-[3-(N-methyl-N-methylsulfonyl-amino)-2-pyridylsulfonyl]-urea 2.9 g (10 mmol) of the compound (II-1) (Example 1) and 1.55 g (10 mmol) of 2-amino-4,6-dimethoxypyrimidine are combined in 30 ml of dichloromethane and refluxed for 8 hours. After the solvent has been removed in vacuo, 4.45 g (100% of theory) of 3-(4,6-dimethoxypyrimidin-2-yl)-1-[3-(N-methyl-N-methylsulfonylamino)-2-pyridylsulfonyl]-urea of m.p. 168°–173° C. (decomp.) are obtained in a purity of approx. 90%.

EXAMPLE 5

3-(4,6-Dimethoxypyrimidin-2-yl)-3-methyl-1-[3-(N-methyl-N-methylsulfonyl-amino)-2-pyridylsulfonyl]-urea (one-pot reaction)

63.0 g (0.17 mol) of 3-butyl-1-[3-(N-methyl-N-methylsulfonylamino)-2-pyridylsulfonyl]urea are suspended in 1 l of chlorobenzene, and the suspension is heated to 70° C. At this temperature, the experiment starts to pass a gentle stream of phosgene into the suspension, and heating is continued for approx. 20 minutes until an internal temperature of 120° C. is reached. After phosgene has been passed in for a further 20 minutes (approx. 50 g (0.5 mol) in total), the lower-boiling components together with approx. 300 ml of chlorobenzene are removed from the reaction mixture by distillation over a period of 30 minutes. After the mixture has cooled to room temperature, 29.0 g (0.17 mol) of 4,6-dimethoxy-2-methylaminopyrimidine dissolved in 500 ml of dichloromethane are added, and the mixture is heated for 7 hours at 40° C. The mixture is cooled, the organic phase is washed with 1×250 ml each of 1N HCl and water, dried and evaporated. After the crude product has been triturated with diethyl ether, 66.6 g (85% of theory) of 3-(4,6-dimethoxypyrimidin-2-yl)-3-methyl-1-[3-(N-methyl-N-methylsulfonyl-amino)-2-pyridyloulfonyl]-urea of m.p. 167°-168° C. (decomp.) remained.

The other compounds of the general formula (I) can be obtained analogously.

I claim:

1. A process for the preparation of compounds of the formula (I)

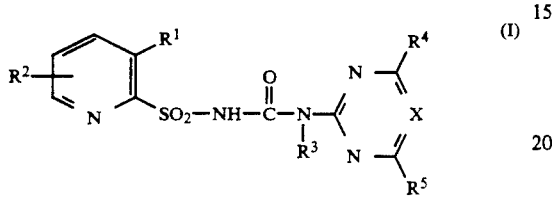

in which
- $R^1$ is $(C_1-C_4)$alkyl, which is unsubstituted or substituted by one or more radicals from the group comprising halogen, hydroxyl, $(C_1-C_4)$alkoxy, $(C_1-C_4)$haloalkoxy and $(C_2-C_8)$alkoxyalkyl, or is $-COR^6$, $(C_1-C_4)$alkylsulfonyl, halogen, $NO_2$, $-ER^7$, $-NR^8R^9$ or $-SO_2NR^{10}OR^{11}$,
- $R^2$ is H, $(C_1-C_3)$alkyl which is unsubstituted or substituted by $(C_1-C_3)$alkoxy, hydroxyl, $(C_1-C_2)$alkylthio or CN, or is $(C_1-C_3)$haloalkyl, halogen, CN, $NO_2$, $(C_1-C_3)$alkoxy, $(C_1-C_3)$alkylthio, $(C_1-C_3)$haloalkoxy, $(C_1-C_3)$alkylamino, di$(C_1-C_3)$alkylamino or $(C_1-C_3)$alkylsulfonyl,
- $R^3$ is H or $CH_3$,
- $R^4$ and $R^5$ independently of one another are $(C_1-C_3)$alkyl, $(C_1-C_3)$alkoxy, $(C_1-C_3)$haloalkyl, $(C_1-C_3)$haloalkoxy, $(C_1-C_3)$alkylthio, halogen, $(C_2-C_5)$alkoxyalkyl or $(C_1-C_3)$alkylamino,
- X is CH or N,
- $R^6$ is H, $-NR^{10}R^{11}$, $-ER^{12}$ or $(C_1-C_4)$alkyl which is unsubstituted or substituted by one or more radicals from the group comprising halogen, $(C_1-C_3)$alkoxy and $(C_1-C_3)$alkylthio,
- E is an oxygen or sulfur atom,
- $R^7$ is $(C_1-C_4)$alkyl which is unsubstituted or substituted by one or more radicals from the group comprising halogen, $(C_1-C_3)$alkoxy, $(C_3-C_4)$alkenyloxy, $(C_3-C_4)$alkynyloxy, $(C_1-C_3)$alkylthio and $[(C_1-C_4)$-alkoxy]-carbonyl, or is $(C_3-C_4)$alkenyl or $(C_3-C_4)$alkynyl,
- $R^8$ is $(C_1-C_4)$alkyl, $(C_1-C_4)$haloalkyl or $(C_2-C_6)$alkoxyalkyl,
- $R^9$ is $(C_1-C_4)$alkylsulfonyl which is unsubstituted or substituted by one or more radicals from the group comprising halogen and $(C_1-C_4)$alkoxy, or $(C_1-C_4)$-haloalkyl
- $R^{10}$ and $R^{11}$ independently of one another are H, $(C_1-C_3)$alkyl, $(C_1-C_3)$haloalkyl, $(C_1-C_2)$alkoxy, $(C_3-C_4)$alkenyl or $(C_3-C_4)$alkynyl, or
- $R^{10}$ and $R^{11}$ together are an alkylene bridge of the formula $-(CH_2)_n-$, in which n is 2, 3, 4 or 5, it being possible for the alkylene bridge to be interrupted by an oxygen atom, and
- $R^{12}$ is $(C_1-C_4)$alkyl which is unsubstituted or substituted by one or more radicals from the group comprising halogen, $(C_1-C_3)$alkoxy, $(C_3-C_4)$alkenyloxy, $(C_3-C_4)$alkynyloxy, phenoxy, $(C_1-C_3)$alkylthio or $[(C_1-C_4)$alkoxy]carbonyl, or is $(C_3-C_4)$alkenyl, $(C_3-C_4)$alkynyl or phenyl, which comprises reacting a zwitterionic 1,1,3-trioxo-1,2,4-thiadiazolo[4,5-a]pyridine of the formula (II)

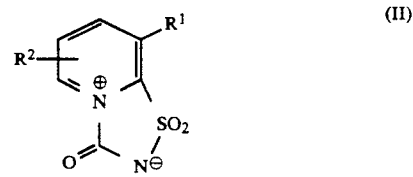

in which $R^1$ and $R^2$ have the same meaning as in formula (I), with an amino heterocycle of the formula (III)

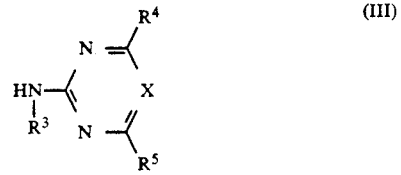

in which $R^3$, $R^4$, $R^5$ and X have the same meaning as in formula (I).

2. The process as claimed in claim 1, wherein
- $R^1$ is $(C_1-C_4)$alkyl, which is unsubstituted or substituted by one or more halogen atoms or one or two hydroxyls or $(C_1-C_4)$alkoxy or by one or more halogen atoms and one or two hydroxyls or $(C_1-C_4)$alkoxy, or is $-COR^6$, $(C_1-C_4)$alkylsulfonyl, halogen or $-NR^8R^9$,
- $R^2$ is H, $(C_1-C_3)$alkyl which is unsubstituted or substituted by $(C_1-C_3)$alkoxy, hydroxyl, $(C_1-C_2)$alkylthio or $-CN$, $(C_1-C_3)$alkylthio, $(C_1-C_3)$haloalkoxy, $(C_1-C_3)$alkylamino or di$(C_1-C_3)$alkylamino,
- $R^3$ is H or $CH_3$,
- $R^4$ and $R^5$ independently of one another are $(C_1-C_2)$alkyl, $(C_1-C_3)$alkoxy, $(C_1-C_2)$haloalkyl, $(C_1-C_2)$haloalkoxy, halogen or $(C_1-C_2)$alkylamino,
- X is CH or N,
- $R^6$ is H, $-ER^{12}$ or $(C_1-C_4)$alkyl,
- E is an oxygen atom,
- $R^8$ is $(C_1-C_4)$alkyl or $(C_1-C_4)$haloalkyl,
- $R^9$ is $(C_1-C_4)$alkylsulfonyl or $(C_1-C_4)$haloalkyl and $R^{12}$ is $(C_1-C_4)$alkyl.

3. The process as claimed in claim 1, wherein the reaction is carried out in an inert organic solvent.

4. The process as claimed in claim 3, wherein an inert organic solvent from the group of aromatic hydrocarbons, halogenated aliphatic and aromatic hydrocarbons, ethers, esters, ketones, nitriles and amides, and mixtures of these, is employed.

5. The process as claimed in claim 3, wherein the reaction is carried out at temperatures from $-10°$ C. up to the boiling point of the solvent.

6. The process as claimed in claim 5, wherein the temperatures are from 0° C. to 80° C.

* * * * *

UNITED STATES PATENT AND TRADEMARK OFFICE
CERTIFICATE OF CORRECTION

PATENT NO. : 5,284,945
DATED : February 8, 1994
INVENTOR(S) : Heinz Kehne

It is certified that error appears in the above-identified patent and that said Letters Patent is hereby corrected as shown below:

Column 2, line 7, change "$(C_1-C_4)$alkoxy, $(C_1-C_4)-$" to --$(C_1-C_4)$ alkoxy, or $(C_1-C_4)-$ --.

Claim 1, Column 7, line 30, change "$-SO_2NR^{10}OR^{11}$" to -- $-SO_2NR^{10}R^{11}$ --.

Signed and Sealed this

Thirtieth Day of August, 1994

Attest:

BRUCE LEHMAN

Attesting Officer        Commissioner of Patents and Trademarks